United States Patent [19]

Bonne et al.

[11] Patent Number: 4,996,431
[45] Date of Patent: * Feb. 26, 1991

[54] SELECTIVE GAS DETECTING APPARATUS

[75] Inventors: Ulrich Bonne, Hopkins; Robert J. Matthys, Minneapolis, both of Minn.

[73] Assignee: Gas Research Institute, Chicago, Ill.

[*] Notice: The portion of the term of this patent subsequent to Sep. 18, 2007 has been disclaimed.

[21] Appl. No.: 308,468

[22] Filed: Feb. 10, 1989

[51] Int. Cl.$^5$ .............................................. G01N 21/61
[52] U.S. Cl. ..................................... 250/343; 250/339
[58] Field of Search ............. 250/343, 339, 345, 338.5

[56] References Cited

U.S. PATENT DOCUMENTS

| | | |
|---|---|---|
| 2,741,703 | 4/1956 | Munday . |
| 3,551,678 | 12/1970 | Mitchell . |
| 3,678,262 | 7/1972 | Herrmann . |
| 3,743,426 | 7/1973 | Steinberg ............................ 250/345 |
| 3,790,797 | 2/1974 | Sternberg et al. ................... 250/345 |
| 3,832,548 | 8/1974 | Wallack ............................... 250/343 |
| 3,893,770 | 7/1975 | Takami et al. ...................... 250/339 |
| 3,897,154 | 7/1975 | Hawes ................................ 250/345 |
| 3,968,367 | 7/1976 | Berg .................................... 250/339 |
| 4,054,384 | 10/1977 | Hawes ................................ 250/345 |
| 4,273,450 | 6/1981 | Watanabe et al. ................... 250/345 |
| 4,297,579 | 10/1981 | Spaeth ................................ 250/343 |
| 4,520,265 | 5/1985 | Griggs et al. ....................... 250/343 |
| 4,543,481 | 9/1985 | Zwick ................................. 250/339 |
| 4,567,366 | 1/1986 | Shinohara ........................... 250/339 |

FOREIGN PATENT DOCUMENTS 1000070 11/1976 Canada ................................ 250/343

Primary Examiner—Carolyn E. Fields
Attorney, Agent, or Firm—Thomas W. Speckman; Douglas H. Pauley

[57] ABSTRACT

A selective gas detecting apparatus for determining the concentration and type of hydrocarbon gas in a gas sample based upon absorption of infrared radiation by the gas sample, the apparatus having two infrared radiation absorption channels with the wavelengths for measurement selected so that one channel at 3.2 microns provides an output signal corresponding to approximately the sum of all hydrocarbons in the gas sample which signal is displayed as an indication of concentration of hydrocarbon gas in the gas sample, and the other channel at 3.4 microns, after essentially being ratioed to the 3.2 micron channel output provides an output signal representative of the type or average type of hydrocarbon in the gas sample, and the ratio of the signal in the two channels is displayed as an indication of the type of hydrocarbon in the gas sample.

20 Claims, 2 Drawing Sheets

SELECTIVE GAS DETECTING APPARATUS

BACKGROUND OF THE INVENTION

This invention relates to gas detecting apparatus, and more particularly, to natural gas detecting apparatus which is able to discriminate between pipeline natural gas, non-pipeline sources of methane, propane, and gasoline vapors.

Utilities which distribute natural gas require reliable gas-leak detectors for use in maintenance of gas supply lines. Existing natural gas detectors are either costly, sensitive and non-selective or low cost, insensitive and non-selective. Non-selective gas detectors respond to any combustible gas. Selective gas detectors are specific to hydrocarbon gases. The two presently most used gas detectors are based on hydrogen flame ionization and on hot wire catalysis. These gas detectors cannot distinguish among different types of hydrocarbons. However, it is necessary to distinguish among different types of hydrocarbons in order to distinguish a pipeline gas from gasoline vapors or sewer or swamp gas and so reduce leak surveyor time wasted on false alarms. Ethane content, if measurable, provides a good means to discriminate between pipeline gas and interfering gasoline vapors and sewer or swamp gases because the later contain practically no ethane, while pipeline gas does, in varying degrees. Gasoline vapors and propane (LP gas) can also generate a false alarm with conventional instruments. However, their infrared absorption is shifted relative to that of methane, as will be described later, as is the basis for this invention to eliminate such false alarms.

In U.S. Pat. No. 4,507,558, there is disclosed a selective detector for natural gas which discriminates between low concentrations of natural gas and other methane sources by measuring the characteristics of the methane/ethane ratio of natural gas as well as by using a combustible gas sensor. The operation of this detector is based on infrared light absorption of methane and ethane in combination with another non-specific combustible gas detector whereby the detector has the ability to detect nonspecifically, the presence of a combustible gas, and to define the nature of the combustible gas. Thus, this natural gas detector utilizes two types of detection including nondispersive infrared detectors and a non-specific combustible detectors such as hot-wire catalytic combustible detector. The detector determines concentration of both methane or ethane irrespective of the concentration of the other gas by using absorption cells placed in front of the detectors. The detector includes a light emitting diode which issues light centered around 3.32 microns and a reference light source which emits light at a wavelength outside of this band. Although this arrangement permits distinguishing among different types of hydrocarbons, the requirement for a hotwire catalytic combustible detector adds cost and complexity to the device and increases power consumption.

It would be desirable to have a natural gas detector which can distinguish among different types of hydrocarbons, and which provides information to the user on the amount and type of combustible gases in the environment.

SUMMARY OF THE INVENTION

It is an object of the invention to provide an improved natural gas detector.

Another object of the invention is to provide a natural gas detector which can distinguish among different types of hydrocarbons.

Another object of the invention is to provide a natural gas detector which provides information to the user on the amount and type of combustible gases in the environment.

A further object of the invention is to provide a natural gas detector which is characterized by simplicity, greater response time and low cost than known discriminating gas detectors.

A further object of the invention is to provide a natural gas detector having the ability to recognize propane leaks, gasoline vapors and swamp or sewer gas.

A further object of the invention is to provide a natural gas detector which provides detection over the entire range of combustible gas without requirement for range switching for its display unit.

These and other objects are achieved by the present invention which has provided a selective gas detecting apparatus for determining the concentration and type or average type of hydrocarbon gas in a gas sample based upon absorption of infrared radiation by the gas sample. The gas detecting apparatus comprises means for passing infrared radiation through the gas sample, infrared radiation detecting means for detecting infrared radiation passed through the gas sample and producing in a first signal channel a first measurement signal indicative of a first wavelength absorbed by the gas sample, and producing in a second signal channel a second measurement signal indicative of a second wavelength absorbed by the gas sample, processing circuit means including first circuit means responsive to said first measurement signal for providing a first output signal corresponding to a first total concentration of hydrocarbons in the gas sample, second circuit means responsive to said second measurement signal for providing a second output signal corresponding to a second total concentration of hydrocarbons in the gas sample, ratio determining means responsive to said first and second output signals for providing a ratio signal corresponding to the ratio of said first and second output signals, said ratio signal being indicative of the type or average type of hydrocarbon, and display means responsive to said second output signal and said ratio signal for providing an indication of the concentration and type or average type of hydrocarbon gas in the gas sample, respectively.

These shifts occur within about 3.0 to 3.8 microns for the fundamental C-H excitation and around 1.6 microns for the first harmonic excitation. All working or main absorption channels use the infrared absorption of light energy by the carbon-hydrogen bonds in hydrocarbons, which shift in intensity in characteristic ways as the structure or chain length of the hydrocarbon changes.

The invention consists of certain novel features and structural details hereinafter fully described, illustrated in the accompanying drawings, and particularly pointed out in the appended claims, it being understood that various changes in the details may be made without departing from the spirit, or sacrificing any of the advantages of the present invention.

DESCRIPTION OF THE DRAWINGS

For the purpose of facilitating and understanding the invention, there is illustrated in the accompanying drawings a preferred embodiment thereof, from an inspection of which, when considered in connection with the following description, the invention, its construction and operation, and many of its advantages will be readily understood and appreciated.

DESCRIPTION OF A PREFERRED EMBODIMENT

Figure 1:
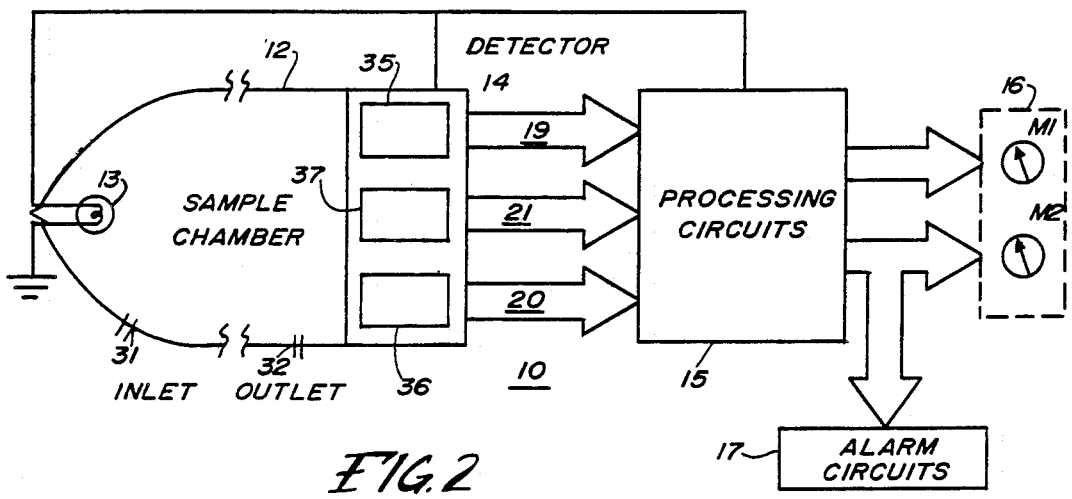
FIG. 1 is a simplified block diagram of the natural gas detector provided by the present invention.

Referring to FIG. 1, the natural gas detector 10 provided by the present invention operates on the basis of absorption of infrared (IR) energy by a gas sample pumped through a gas sample chamber defined by an optical cell 12. The natural gas detector 10 includes a detection arrangement in which gas concentration is determined using an appropriate optical cell 12 which defines a gas sample optical path length of 50 centimeters in the exemplary embodiment, a source of infrared radiation 13, an infrared radiation detecting circuit 14, processing circuits 15, a display unit 16 including analog meters M1 and M2, and an alarm circuit 17.

In accordance with one aspect of the invention, the natural gas detector 10 uses two signal channels 19 and 20 and two infrared wavelengths for measurement of absorption of methane and ethane in determining the amount and type or source of combustible gases in an environment. In the preferred embodiment, one wavelength is 3.2±0.1 microns and the other wavelength is 3.4±0.1 microns. A reference signal at a wavelength of 2.9 (or 3.9) +0.1 microns is provided in a third channel 21. The wavelengths for measurement of the two channels at 3.2 microns and 3.4 microns are selected so that one infrared absorption channel 19 (at 3.2 microns) provides a measurement signal corresponding to the total concentration or sum of ethane and methane and other hydrocarbons in the gas sample. The other infrared absorption channel 20 (at 3.4 microns) provides a second measurement of total hydrocarbon concentration in the gas sample. For a gas mixture containing only air, methane and ethane, the processing circuits 15 determine the percentage of ethane in such a natural gas simulant. With real natural gas, the detector provides a first output signal indicating on the one hand, the sum of all hydrocarbon concentrations in the gas sample, and a second output signal indicating, on the one hand, the presence of swamp or sewer gas, natural or propane in the gas sample. The output signals are applied to the display unit 16. The gas measurement information displayed by the gas detector 10 includes total gas concentration which is represented by the sum of all hydrocarbons, including methane and ethane and displayed by the first meter M1, and the gas type or average gas type i.e. methane (sewer) gas, pipeline (natural) gas, or concentrations of propane gas or gasoline vapors, displayed by the second meter M2.

More specifically, the optical chamber 12 is interposed between the source 13 of the infrared radiation and the detecting circuit 14 and has a gas inlet 31 near one end thereof and a gas outlet 32 near the opposite end thereof. The infrared radiation source may be a tungsten subminiature light bulb, for example.

The detecting circuit 14 includes a detector 35 associated with infrared absorption channel 19, a detector 36 associated with infrared absorption channel 20 and a reference detector 37 associated with both absorption channels 19 and 20. The detectors 35–37 may each comprise a PbSe sensor. The signal in absorption channel 19 is applied to an analog meter M1 which provides a reading indicative of total gas concentration, or the amount of methane, ethane and other hydrocarbons in air. The signal in absorption channel 19 is combined with the signal in absorption channel 20 to provide an output which is displayed by analog meter M2 indicative of the type of hydrocarbon in the gas sample under test, with a small reading signifying swamp or sewer gas, a low to mid-scale reading being representative of natural gas, a midscale reading indicating propane and a reading near full scale signifying gasoline vapors. In accordance with a feature of the invention, the meters M1 and M2 have logarithmic scales so that range switching is not required.

Figure 2:
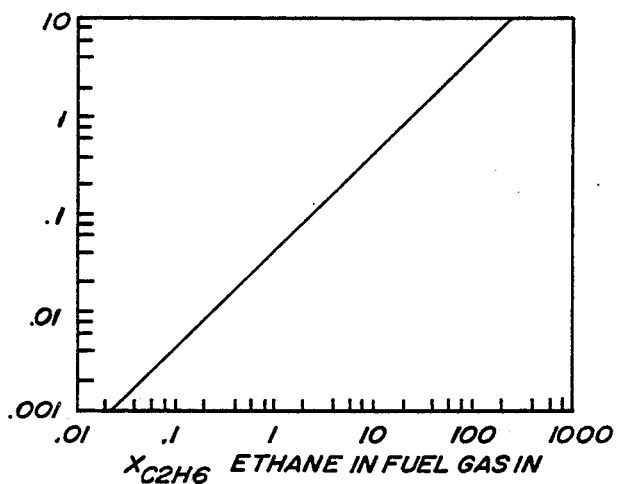
FIG. 2 is a graphical representation of ethane concentration in mixtures with methane compared to a ratio of infrared absorption signals at different wavelengths.

Referring to FIG. 2, there is illustrated a relationship between percent of ethane in a fuel gas sample as a function of the ratio of the absorption signal at 3.4 microns to that at 3.2 microns. The scales are logarithmic and accordingly, the data provides a straight line display.

Figure 3:
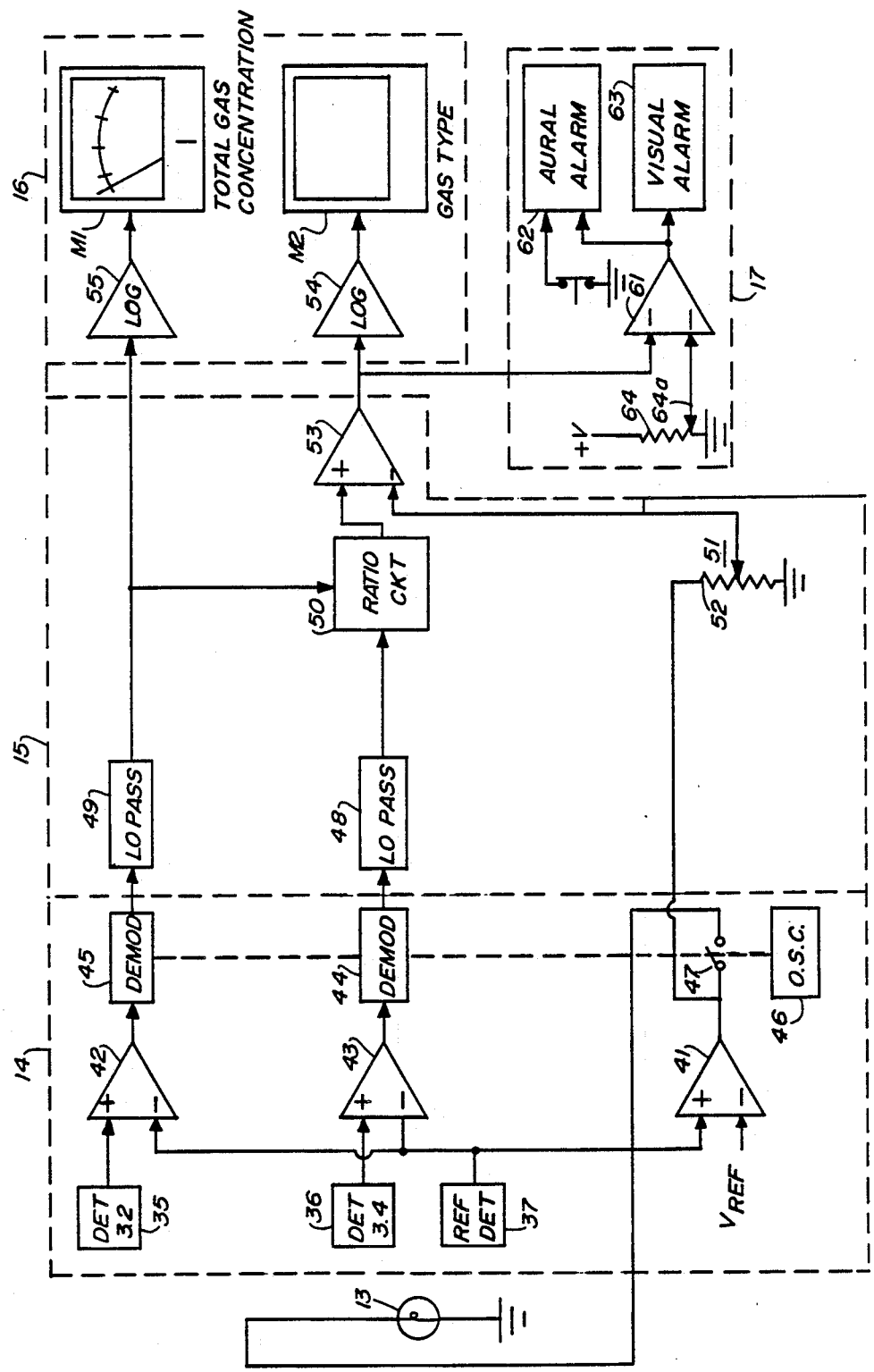
FIG. 3 is a detailed block diagram of the natural gas detector provided by the present invention.

Considering the circuits of the gas detector 10 in more detail, with reference to FIG. 3, the detecting circuit 14 further includes three operational amplifier circuits 41, 42 and 43, each connected for operation as a subtracting circuit, a demodulating circuit 44, a demodulating circuit 45, an oscillator circuit 46 and a switch 47.

The processing circuits 15 include a low pass filter 48, a low pass filter 49, a ratio determining circuit 50 and a reference circuit 51 including a potentiometer 52, and an operational amplifier circuit 53 which is connected for operation as a subtracting circuit.

The display unit 16, further includes a logarithmic amplifier 54 associated with meter M2 and a logarithmic amplifier 55 associated with meter M1.

Amplifier 41 has its non-inverting input connected to a source of reference potential VREF and its inverting connected to the output of the reference detector 37. The source of infrared radiation 13 is connected to the output of amplifier 41 in series with switch 47. The oscillator circuit 46 generates a signal at 10 Hz which controls the operation of switch 47 to provide intermittent driver at a 10 Hz rate for the tungsten lamp which comprises the source of infrared radiation 13.

Absorption channel 19 includes amplifier 42 which is connected for operation as a subtracting circuit, demodulating circuit 45, low pass filter 49 and a logarithmic amplifier 55. Amplifier 43 has its non-inverting input connected to the output of detector 35 and its inverting input connected to the output of the reference detector 37. The output of the amplifier circuit 43 is connected to the demodulating circuit 45 which receives the 10 Hz phase signal from the oscillator 46. The signal output of the demodulating circuit 45 is passed through the low-pass filter 49, which is set at 1 Hz, for eliminating the pulsing effect of the 10 Hz drive, providing a DC output signal which is applied to the logarithmic amplifier 55. The logarithmic amplifier 55 responsively generates outputs a signal representing the concentration of methane and ethane in air. The signal output of the logarithmic amplifier 55 is applied as a drive signal to the analog meter M1.

Figure 4:
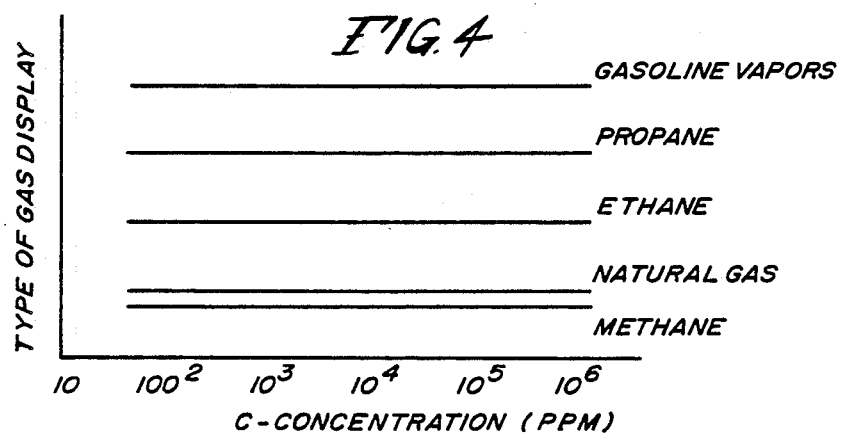
FIG. 4 is a graphical representation of the type of gas display of the detector versus individual gas concentrations.

Infrared absorption channel 20 includes operational amplifier 42 which is connected for operation as a subtracting circuit, demodulating circuit 44, low-pass filter 48, a ratio determining circuit 50, operational amplifier 53 of reference circuit 51 and logarithmic amplifier 54. The amplifier 43 has its non-inverting input connected to the output of detector 36 and its inverting input connected to the output of the reference detector 37. The output of amplifier 42 is connected to the input of demodulating circuit 44 which receives a phase signal at 10 Hz from the oscillator 46. The signal output of the demodulating circuit 44 is passed through low-pass filter 48 which attenuates above 1 Hz to provide a DC output signal. The ratio determining circuit 50 produces a ratio signal S corresponding to the quotient or ratio of the signal in channel 20 to the signal in channel 19. The ratio signal produced by of ratio circuit 50 is applied to the noninverting input of subtracting circuit 53 which receives at its inverting input an offset signal $1/k_1$. The value of the offset is selected to cause the value of the ratio signal S to be zero when the gas sample is methane. In an exemplary embodiment, the value of $k_1$ was 1.333. The signal output of amplifier 53 is applied to the logarithmic amplifier 54 which provides drive signals for meter M2 which signals are indicative of the type or average type of hydrocarbon gas in air and largely independent of the concentration of the gas, as indicated by FIG. 4. The scale of meter M2 has three defined regions A, B, and C for signifying detection of swamp gas, natural gas and propane/gasoline vapors, respectively.

The alarm circuit 17 includes a comparator 61, an audible alarm device 62 and a visual alarm device 63 which are commonly connected to the output of the comparator 61. The comparator circuit 61 has its inverting input connected to the wiper 64a of to receive a reference signal generated by potentiometer 64 and its non-inverting input connected to the output of ratio determining circuit 50 of the absorption channel 20. The reference level is set by adjusting potentiometer 64 to provide an alarm whenever a minimum amount of ethane is detected by the gas detector 10.

Referring to FIG. 3, in use, the tungsten light which comprises infrared radiation source 13 is driven by the oscillator 46 at a 10 Hz rate. The gas sample being tested is pumped through the sample chamber 12 (FIG. 1) from its inlet 31 to its outlet 32. The light output is directed through the sample chamber 12 (FIG. 1) which contains the gas sample being analyzed. Amplifier 41 and reference infrared detector 37 form a compensation circuit, supplying a signal to the inverting inputs of amplifiers 42 and 43, as well as to amplifier 41, to compensate for variations in the infrared radiation level produced by the source 13. Demodulating circuits 44 and 45 synchronize measurement by the detectors 35-37 of absorption of infrared radiation by the gas sample with the "on" time of the tungsten lamp which comprises the infrared radiation source. The detectors 35, 36 and 37 provide measurement signals indicative of the absorption of infrared radiation at wavelengths 3.2 microns, 3.4 microns and 2.9 (or 3.9) microns, respectively. Low pass filters 49 and 48 eliminate the effect of the 10 Hz electronic chopping of the light output of the source 13 on the detection signals in signal channels 19 and 20. In absorption channel 19 passed through the low-pass filter 49, which is a DC signal representative of the sum of methane and ethane in the gas sample is applied to amplifier 55. The logarithm of the measurement signal is obtained by the logarithmic amplifier 55 and applied to meter M1 which indicates concentration in parts per million PPM.

In absorption channel 20, the measurement signal passed through low-pass filter 48 which is a DC signal indicative of the difference in the concentration of methane and ethane in the gas sample is applied to ratio determining circuit 50 which also receives the measurement signal in channel 19. This measurement signal in channel 20 is divide by the measurement signal in absorption channel 19, the resultant ratio signal being representative of the type of hydrocarbon in the gas sample. The factor $1/k_1$ is subtracted from the ratio signal by subtracting circuit 53. The logarithm of the resultant ratio signal is obtained by logarithmic amplifier 54 and applied to meter M2. A small reading, 0-0.1 percent on the panel meter M2 that the gas sample is signifies swamp or sewer gas. An intermediate reading 1-10 percent is indicative that the gas sample is natural gas. A reading above 20 percent or 30 percent is indicative of that the gas sample contains concentrations of propane or gasoline vapors.

We claim:

1. A selective gas detecting apparatus for determining a concentration and type or average type of hydrocarbon gas in a gas sample based upon absorption of infrared radiation by the gas sample, comprising: means for passing infrared radiation through the gas sample, infrared radiation detecting means for detecting infrared radiation passed through the gas sample and producing in a first signal channel a first measurement signal indicative of a first wavelength absorbed by the gas sample, and producing in a second signal channel a second measurement signal indicative of a second wavelength absorbed by the gas sample, processing circuit means including first circuit means responsive to said first measurement signal for providing a first output signal corresponding to a first total concentration of hydrocarbons in the gas sample, second circuit means responsive to said second measurement signal for providing a second output signal corresponding to a second total concentration of hydrocarbons in the gas sample, ratio determining means responsive to said first and second output signals for providing a ratio signal corresponding to the ratio of said first and second output signals, said ratio signal being indicative of the type or average type of hydrocarbon gas, and display means responsive to said first output signal and said ratio signal for providing an indication of the concentration and type or average type of hydrocarbon gas in the gas sample, respectively.

2. A gas detecting apparatus according to claim 1, wherein said first wavelength is 3.2±0.1 microns and said second wavelength is 3.4±0.1 microns.

3. A gas detecting apparatus according to claim 2, wherein said infrared radiation detecting means produces a reference measurement signal indicative of a third wavelength absorbed by the gas sample, said reference measurement signal being applied to said first and second circuit means for generating said first and second output signals.

4. A gas detecting apparatus according to claim 3, wherein said third wavelength is 2.9±0.1 microns.

5. A gas detecting apparatus according to claim 2, wherein said third wavelength is 3.9±0.1 microns.

6. A gas detecting apparatus according to claim 3, wherein said processing circuit means further comprises offset means for adjusting said ratio signal to be a preselected value when said ratio signal indicates that the type of hydrocarbon is methane.

7. A gas detecting apparatus according to claim 6, wherein said offset means includes means for producing an offset signal and circuit means for subtracting said offset signal from said ratio signal at the output of said ratio determining means.

8. A gas detecting apparatus according to claim 3, wherein said display means comprises first and second analog meters and first and second function circuit means, said first function circuit means being interposed between said ratio determining means and said first meter and responsive to said ratio signal for providing a signal corresponding to the logarithm of said ratio signal for driving said first meter, and said second function circuit means being interposed between said first circuit means and said second meter and responsive to said second output signal for providing a signal corresponding to the logarithm of said second output signal for driving said second meter.

9. A gas detecting apparatus according to claim 3, further comprising alarm means responsive to said ratio signal for providing an indication whenever a measured concentration of ethane is below a preselected level.

10. A gas detecting apparatus according to claim 4, wherein said infrared radiation detecting means comprises first, second and third infrared detectors responsive to infrared radiation at 3.4 microns, 3.2 microns, and 2.9 microns, respectively, first combining circuit means for combining signal outputs of said first and third detectors to produce said first measurement signal, and second combining circuit means for combining signal outputs of said second and third detectors for producing said second measurement signal.

11. A gas detecting apparatus according to claim 3, wherein said first and second circuit means each comprise a low pass filter circuit and said ratio determining means comprises a function circuit providing a signal output corresponding to a quotient of said first and second output signals.

12. A gas detecting apparatus according to claim 11, wherein said display means comprises first and second analog meters and first and second function circuit means, said first function circuit means being interposed between said ratio determining means and said first meter and responsive to said ratio signal for providing a signal corresponding to a logarithm of said ratio signal for driving said first meter, and said second function circuit means being interposed between said first circuit means and said second meter and responsive to said second output signal for providing a signal corresponding to the logarithm of said second output signal for driving said second meter.

13. A gas detecting apparatus according to claim 12, wherein said first meter has a scale divided into low, intermediate and high reading portions to indicate that the type of hydrocarbon is swamp gas, or natural gas, propane or gasoline vapors, respectively.

14. A selective gas detecting apparatus for determining the concentration and type or average type of hydrocarbon gas in a gas sample based upon absorption of infrared radiation by the gas sample comprising: means for passing infrared radiation through the gas sample, infrared detecting means for detecting infrared radiation passed through the gas sample including a first infrared detector producing a first detection signal indicative of a first wavelength absorbed by the gas sample, a second infrared detector producing a second detection signal indicative of a second wavelength absorbed by the gas sample, and a reference infrared detector producing a reference signal indicative of a third wavelength absorbed by the gas sample, first signal combining circuit means for combining said reference signal with said first detection signal to produce a first measurement signal indicative of said first wavelength absorbed by the gas sample, second signal combining circuit means for combining said reference signal with said second detection to produce a second measurement signal indicative of said second wavelength absorbed by the gas sample, processing circuit means including first circuit means responsive to said first measurement signal for providing a first output signal corresponding to a first total concentration of hydrocarbons in the gas sample, second circuit means responsive to said second measurement signal for providing a second output signal corresponding to a second total concentration of hydrocarbons in the gas sample, ratio determining means responsive to said first and second output signals for providing a ratio signal corresponding to the ratio of said first and second output signals, said ratio signal being indicative of the type or average type of hydrocarbon gas, and display means responsive to said second output signal and said ratio signal for providing an indication of the concentration and type or average type of hydrocarbon gas in the gas sample, respectively.

15. A gas detecting apparatus according to claim 14, wherein said first wavelength is 3.2 microns, said second wavelength is 3.4 microns and said third wavelength is 3.9 microns.

16. A gas detecting apparatus according to claim 15, wherein said first wavelength is 3.2 microns, said second wavelength is 3.4 microns and said third wavelength is 2.9 microns.

17. A gas detecting apparatus according to claim 16, wherein said processing circuit means further comprises offset means for adjusting said ratio signal to be a preselected value when said ratio signal indicates that the type of hydrocarbon is methane.

18. A gas detecting apparatus according to claim 17, wherein said offset means includes means for producing an offset signal and circuit means for subtracting said offset signal from said ratio signal at the output of said ratio determining means.

19. A gas detecting apparatus according to claim 16, further comprising alarm means responsive to said ratio signal for providing an indication whenever the measured concentration of ethane is below a preselected level.

20. A method of determining a concentration and type or average type of hydrocarbon gas in a gas sample comprising: passing infrared radiation through the gas sample, detecting infrared radiation passed through the gas sample, producing in a first signal channel a first measurement signal indicative of a first wavelength absorbed by the gas sample and corresponding to a first total concentration of hydrocarbons in the gas sample, producing in a second signal channel a second measurement signal indicative of a second wavelength absorbed by the gas sample and corresponding to a second total concentration of hydrocarbons in the gas sample, obtaining a ratio of the first and second measurement signals to produce a ratio signal indicative of the type or average of hydrocarbon gas and applying the second measurement signal and the ratio signal to first and second analog meters to provide an indication of the concentration and type or average of hydrocarbon gas, respectively, in the gas sample.

* * * * *